United States Patent [19]
Withers et al.

[11] Patent Number: 5,323,719
[45] Date of Patent: * Jun. 28, 1994

[54] CONTAMINATED WASTES DISPOSAL SYSTEM

[75] Inventors: L. Andrew Withers, Atlanta; David W. Hughes, Chamblee, both of Ga.

[73] Assignee: McDonald, Withers & Hughes, Inc., Atlanta, Ga.

[*] Notice: The portion of the term of this patent subsequent to Nov. 17, 2009 has been disclaimed.

[21] Appl. No.: 890,022

[22] Filed: May 28, 1992

Related U.S. Application Data

[63] Continuation-in-part of Ser. No. 699,915, May 14, 1991, Pat. No. 5,167,193, and a continuation-in-part of Ser. No. 737,427, Jul. 29, 1991, Pat. No. 5,163,375.

[51] Int. Cl.$^5$ .................................................. F23G 7/04
[52] U.S. Cl. .................................... 110/346; 110/238; 110/246; 206/366; 206/570
[58] Field of Search ............... 110/246, 346, 341, 238; 110/246; 206/366, 570

[56] References Cited
U.S. PATENT DOCUMENTS
4,850,290  7/1989  Benoit et al. .................. 110/246

Primary Examiner—Henry C. Yuen
Attorney, Agent, or Firm—Hopkins & Thomas

[57] ABSTRACT

The system (10) for collecting and disposing of contaminated waste products such as medical sharps and other medical wastes includes a housing (11) and its telescopic cover (9) which are fabricated of biodegradable and combustible material such as natural cellulose and non-natural cellulose. An absorbent biodegradable and combustible absorption package (30) or insert (35) can be placed in the bottom of the holding chamber (12) for absorbing any liquids emitted from the sharps and other wastes, and for enhancing the combustion of the medical sharps and other wastes when the housing is placed in a furnace. When the housing is burned it evolves no more than trace levels of sulfur or chlorine and yields substantially only biodegradable ash.

3 Claims, 3 Drawing Sheets

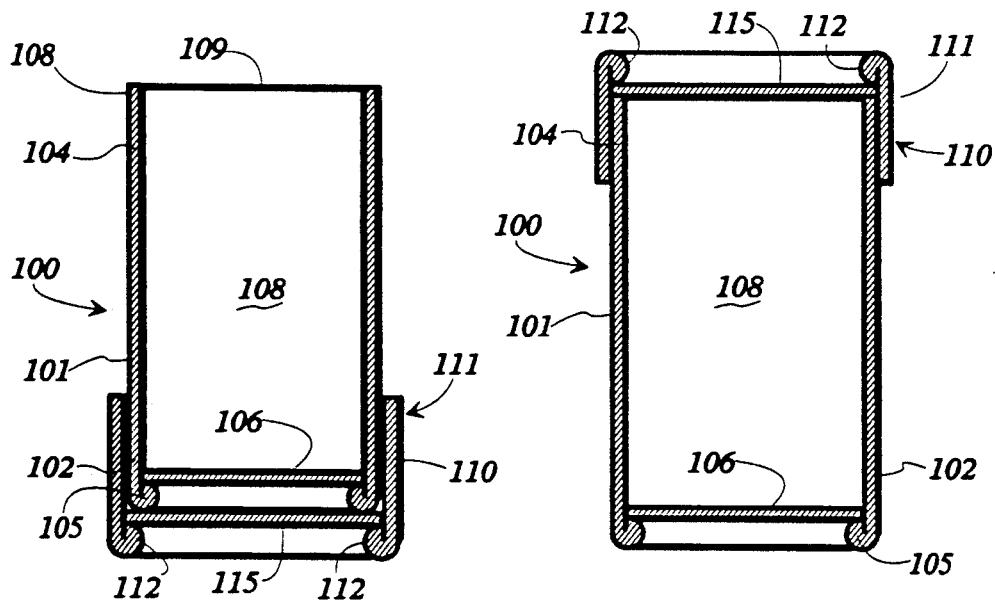
FIG 10  FIG 11
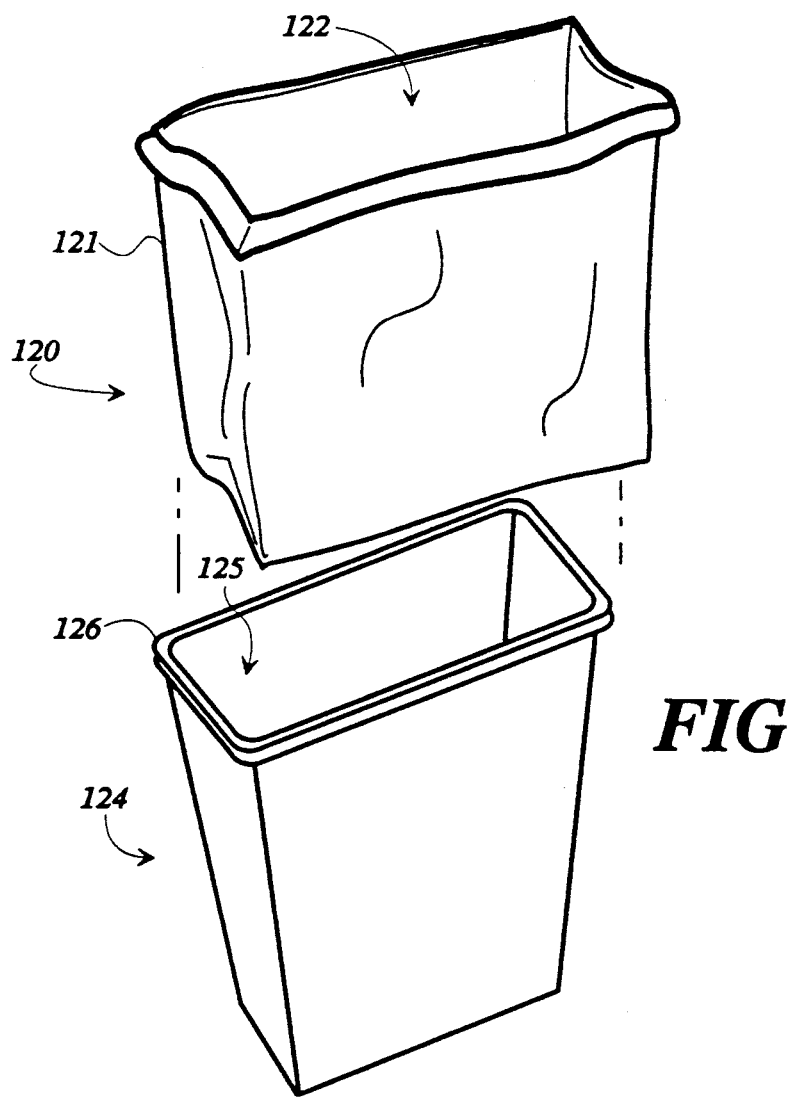
FIG 12

CONTAMINATED WASTES DISPOSAL SYSTEM

CROSS REFERENCE

This is a continuation-in-part of prior U.S. Pat. applications Ser. Nos. 699,915 filed May 14, 1991 U.S. Pat. Nos. 5,167,193 and 737,427 filed Jul. 29, 1991, U.S. Pat. No. 5,163,375.

FIELD OF THE INVENTION

The present invention relates in general to a system for disposing of contaminated wastes. More particularly, the invention relates to a system for collecting and disposing of medical sharps and other medical wastes in a home or hospital environment.

BACKGROUND OF THE INVENTION

The term "medical sharps" generally is defined as medical instruments having a sharp cutting edge or a sharp point. In the medical environment, sharps comprise hypodermic needles, syringes, scalpel blades, and the like. After use, medical sharps are considered contaminated wastes and must be disposed of. Other contaminated medical wastes, including chemotherapy, pathological and dental wastes, comprise surgical tubing, washcloths, surgical gloves, masks, garments, drapes, cultures of infectious agents, and the like. Additionally, other types of wastes include surgical "kit packs" for performing specific surgical procedures, whereby after use in an operation, such kit packs are considered contaminated wastes. After use, medical sharps and other contaminated medical wastes must be safely collected and disposed of without creating a hazard for the hospital personnel, patients, or visitors of a medical care facility, or for members of the family when used in the home.

Typically in the home environment, medical wastes such as expired medication, medical gauze, and medical tape can be safely discarded in a regular household trash can. However, in other situations where the patient receives medical injections away from the medical care facility, such as a diabetic patient who must monitor his or her blood sugar level and then administer self-injections of insulin, the used insulin needle syringes must be safely disposed of so as to avoid presenting a hazard to other members of the family or community. Also, other diseases require the frequent use of needle syringes in the home. Presently, none of the known prior art discloses a collector or receptor for safely discarding contaminated or hazardous medical wastes such as insulin syringes of a diabetic patient in a home environment.

When medical sharps or surgical "kit packs" are being used in a hospital, typically the hospital protocol is to use and immediately dispose of these medical wastes in receptacles, such as in plastic, wall-mounted receptacles or in large receptors placed on the floor having an open top, otherwise known as "kick buckets". Typically the medical waste receptacles are placed in strategic locations throughout the hospital or other medical treatment facility, such as in the patient's rooms, in the hall outside the patient's room, in treatment rooms, operating rooms, and emergency rooms, so as to be available for receiving the medical wastes immediately and conveniently after use by the nurse, physician, or other medical personnel. Additionally, the kick buckets are generally placed in operating rooms and emergency rooms for receiving large volumes of various types of medical wastes. The receptacles must be suitably sized and shaped to receive the anticipated amount of medical waste over a period of time, depending on the protocol of the medical facility, and the receptacles must easily receive yet securely and safely retain the medical waste so as to avoid presenting a hazard to children or to disoriented patients or to curious visitors.

After these receptacles are filled with medical wastes, they are collected for disposal, usually for burning in an incinerator. The collection procedure usually requires housekeeping personnel to move about the hospital with a plastic bag or other relatively large container and to place the filled receptacles in the bag, and to replace the used receptacles with new empty receptacles, for example by dismounting the used plastic receptacles from their wall brackets and mounting the new receptacles in the wall brackets. After replacement and collection of the medical waste receptacles, the collected receptacles are securely packaged in a larger container such as a plastic bag or cardboard box and the bag or box is carried to a burn facility.

During the containment and collection procedure of medical wastes, there is the hazard that the medical waste materials will contaminate the personnel who are handling or are exposed to the wastes. Experience demonstrates that accidents caused by the medical waste materials through skin scratch or puncture and other exposure are occasional causes of injury to personnel and such accidents are a considerable expense to hospitals and insurance companies.

For example, when the used receptacles that are filled with medical wastes are being removed from their holders or being transported, the needle of a syringe can protrude from or escape from its individual receptacle and scratch or puncture the personnel handling the receptacle.

Therefore, it is highly desirable that the use-and-dispose method provides for safe containment and collection of the medical sharps and other wastes within the home and the hospital environment by providing a collector which is puncture resistant and leak resistant.

Another problem can be created during disposal of the medical wastes. The usual method of disposal is incineration, whereby the medical wastes are converted into ash for delivery to a landfill, etc. The disposal systems for the medical wastes range from on-site incinerators to contract disposal services which transport the medical wastes to off-site burn facilities. Generally, the treatment plants incinerate the collectors and the medical wastes contained in the collectors and then bury the residue of the burned medical wastes and collectors in a landfill.

An incineration technique is especially advantageous for disintegrating contaminated sharps and other pathological wastes, because incineration has the ability to convert the contaminated substances into a non-contaminated ash. However, when certain materials such as plastics of a syringe are burned, ashes from the incineration of these materials can become a partially pyrolized plastic residue, which is essentially a tar ash or residue which when buried in a landfill, is non-biodegradable waste. Although the ashes of plastic syringes and some other types of plastic wastes will be delivered to landfills, it is highly desirable to avoid the use of plastic collectors for these wastes, because when plastic collectors are burned they can emit toxic gases to the atmosphere and create even more non-biodegradable ash, which is an undesirable additive to a landfill.

Thus, it would be advantageous to provide a disposable collector system for collecting and disposing of medical sharps and other medical wastes which is safe and efficient to use, which is biodegradable, which can be specifically constructed for home use by a diabetic, and which can be incinerated without the evolution of any substantial toxic gases and which when burned aids in rendering the wastes. It also would be desirable to fabricate the collector of a combustible material that yields substantially only biodegradable ash upon incineration and to adjust the mass of the collector with respect to the anticipated mass of the wastes to be collected in the collector so as to control the heat emitted by the collector upon burning so as to render the contained wastes in to ash. Thus, the ratio of the resulting biodegradable ash of the collector with respect to the non-biodegradable ash of the waste can be controlled when the collector and its wastes are burned.

SUMMARY OF THE INVENTION

Briefly described, the present invention comprises a system for collecting and disposing of medical sharps and other medical wastes, which provides a leak resistant, combustible, and biodegradable housing including a closed lower portion and an upper portion with an opening for receiving medical wastes. In one embodiment of the invention the upper portion of the housing includes a lid with an openable area, such as a scored portion of the housing for yieldably opening the upper portion of the housing while normally maintaining the housing closed. A wall bracket is provided for mounting the housing to a wall of a building for releasably holding the housing in a firm and safe condition.

Additionally, the collector housing is formed of a renewable resource or non petroleum-based material, which when incinerated will yield substantially only a biodegradable ash, otherwise known as mineral-ash. In a preferred embodiment of the invention, the entire housing is fabricated of material possessing combustible and biodegradable characteristics. When incinerated in a furnace environment the collector initially retains its medical wastes and the heat of combustion of the collector adds to the heat used to render the medical wastes in the collector housing.

One embodiment of the invention is specifically sized and shaped to receive an anticipated amount of insulin syringes in the home environment of a diabetic patient. Additionally, an embodiment has the option of being attached if desired, such as by adhesives, to horizontal or other selected surfaces of different rooms throughout the home so as to be conveniently located for disposal of the used syringes after each self injection of insulin. This embodiment also provides a designated place to collect and dispose of the used insulin syringes in the home environment.

In another embodiment of the invention, a wall-mounted head or lid releasably supports the disposable collector housing, and the wall mounted lid of the housing receives and passes the medical wastes into its collector housing. This head is formed of a clear material such as glass or any other material with glass-like qualities wherein the user can view inside the housing as the medical wastes are collected and fill up the housing. Additionally, the head is cleanable and non-stainable.

Another embodiment of the present invention provides an absorbent material located inside a collector housing for absorbing any fluid emitted from or residual on the discarded medical wastes. A preferred form of the absorbent material possesses all or a combination of absorbent, cellulosic, antimicrobial, antibacterial, antifungal, biodegradable, and combustible properties, whereby any residual fluid inside the collector housing tends to be preferentially absorbed and dispersed in the absorbent material to protect personnel from coming into direct contact with the liquid medical wastes, and when incinerated, the dispersion of the fluids in the absorbent material tends to enhance combustion of the discarded medical wastes.

In another embodiment of this invention, the housing comprises a dual-wall construction, wherein the material of the housing also is fabricated of a combustible and biodegradable material. In addition, this embodiment provides an effective approach to controlling the wall thickness of the housing, which substantially increases the puncture-resistance factor of the housing. The dual-wall construction can be combined with an absorptive package or insert within the housing to further improve the leak resistance of the system for collecting and disposing of medical wastes.

It is therefore an object of the present invention to provide an apparatus which collects, contains, and disposes of medical wastes in a safe, convenient, and inexpensive manner.

Another object of the present invention is to provide a collector housing which can be suitably sized, shaped, and placed to receive an anticipated amount of insulin syringes in the home environment of a diabetic.

It is yet another object of the present invention to provide a collector housing which is combustible and biodegradable and formed from a renewable resource, otherwise known as a non-petroleum-based material.

A further object of the present invention is to provide a collector housing particularly advantageous for use when discarding chemotherapy, pathological, and other non-sharp medical wastes.

A further object of the present invention is to provide such a system for collecting and disposing of medical sharps, whereby the housing itself is puncture resistant, leak resistant, rigid, and combustible for safe containment and effective treatment of medical sharps.

It is yet another object of the present invention to provide a collector housing for collecting and disposing of medical wastes in a safe and economical manner, and to provide within the housing an absorptive, antimicrobial, antifungal, antibacterial material whereby when wastes are deposited into the housing, any fluid emitted from the wastes will be absorbed and disinfected.

A further object of this invention is to provide a collector housing for collecting and disposing of medical wastes wherein an absorbent and combustible material is contained within the housing adjacent the space where the medical wastes are collected.

Another object of this invention is to provide a system for collecting and disposing of medical wastes, such as syringes used for injecting medication, whereby the system comprises a combustible housing that, upon combustion, fully renders the medical waste within the environment of a furnace.

It is another object of the present invention to provide such a system of collecting and disposing of medical wastes wherein the housing for collecting the medical wastes is of appropriate mass and rigidity during initial burning to substantially retain the medical wastes therein, until the wastes combust and begin to be reduced to ash.

Another object of the present invention is to provide such a collector system in which the housing itself comprises a combustible material that, upon combustion leaves substantially only biodegradable ash.

A further object of the present invention is to provide a system for collecting and disposing of medical wastes wherein the entire housing is fabricated of a clean burning combustible material that, upon combustion, emits gases which are substantially free of sulfur or chlorine.

A more complete understanding of the present invention will be had by those skilled in the art, as well as an appreciation of additional advantages, which will become apparent upon reading the detailed description of the preferred embodiment and examining the drawings, the following of which is a brief description.

BRIEF DESCRIPTION OF THE DRAWINGS

FIG. 10 is a side cross-sectional view of another embodiment of the system for collecting and disposing of medical wastes, having an open top, with the cover mounted for storage on the bottom.

FIG. 11 is a side cross-sectional view of the embodiment of FIG. 10, with the cover closing the top opening.

FIG. 12 is an exploded perspective view of another embodiment of the system for collecting and disposing of medical wastes.

DETAILED DESCRIPTION

Figure 1:
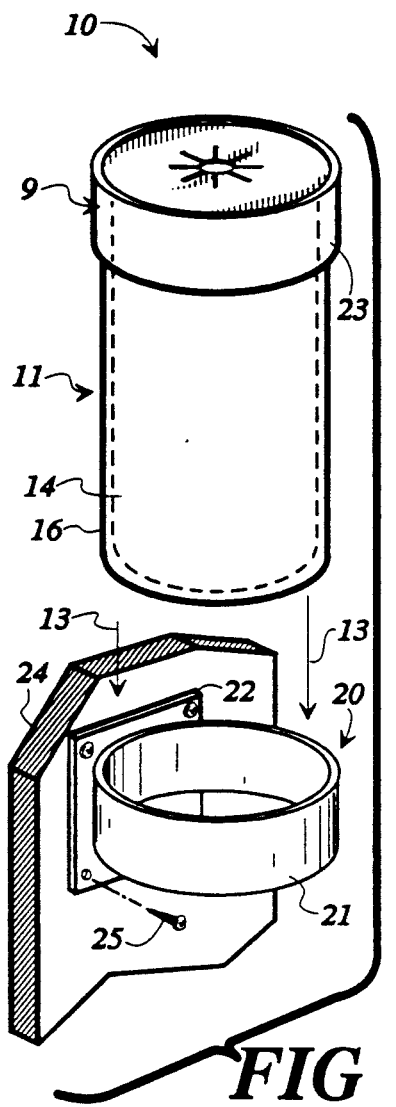
FIG. 1 is a perspective view of the system for collecting and disposing of medical wastes and its wall holder, showing how the housing of the system fits into the wall bracket.
Figure 2:
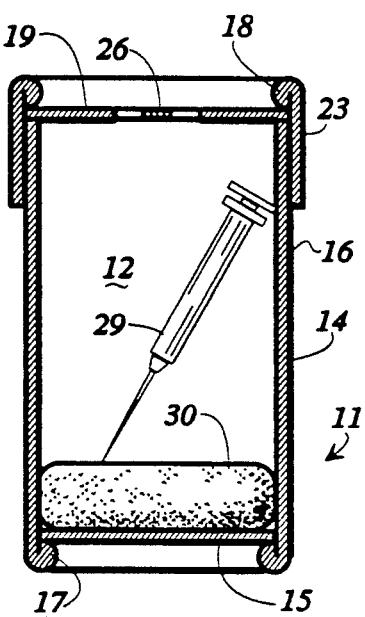
FIG. 2 is a side cross-sectional view of the system for collecting and disposing of medical wastes of FIG. 1, showing a syringe that has been deposited in the collector housing.
Figure 3:
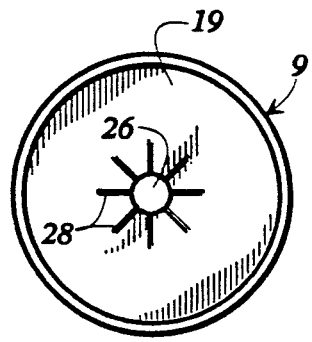
FIG. 3 is a top view of the circular lid of the system for collecting and disposing of medical wastes of FIG. 1.

Referring now in more detail to the drawings, in which like numerals indicate like parts throughout the several views, FIGS. 1-3 illustrate the system 10 for collecting and disposing of medical wastes which includes a cylindrical housing 11 and its wall mount 20, according to the present invention. The housing 11 is shown separated from a wall mount 20 and ready for insertion into a circular sleeve 21 of the wall mount 20 as indicated by the downward directional arrows 13. The wall mount 20 comprises a mounting bracket 22, preferably attached to a wall 24 by multiple screws 25 which extends through openings of the bracket into the wall of the building structure, and the mounting bracket 22 supports the circular sleeve 21 in an upright attitude.

The housing 11 comprises an upper telescoping cover 9 and a lower cylindrical body 14. The upper telescopic cover can be attached, such as by adhesive connection, to the cylindrical body of the housing which includes a cylindrical side wall 16 with the lower end portion of the side wall turned inwardly to form a circular flange or seat 17 (FIG. 2) and the bottom wall or "plug" 15 is positioned inside the side wall and is supported on the seat 17. Lower cylindrical body 14 and its bottom wall 15 define a holding chamber 12 which is open at its upper end. An absorptive insert in the form of an absorption pack 30 resting on bottom wall 15 acts to absorb and disperse liquids throughout the absorption pack and also can be partially penetrated by syringe needles and other medical sharps. The configuration and density of the material of the absorptive insert are selected to absorb the anticipated types and amounts of liquids from the syringes and other items to be placed in the housing 11. Additionally, the absorptive material of the insert can be more absorptive than the material of the housing 11.

The telescoping cover 9 includes a cylindrical side wall 23 which is of sufficient internal breadth to telescopically fit over the upper end of the cylindrical side wall 16 of the lower cylindrical body 14 with a tight fit, and the telescoping cover 9 is of a diameter larger than the space defined by the sleeve 21 of the mounting bracket 22 so that when the housing 11 is moved down into the circular sleeve 21 of the wall mount 20 the cover 9 supports the cylindrical housing 11 in the mounting bracket. The telescoping cover 9 has on its uppermost portion, upper inwardly projecting circular seat 18 and a top wall or "plug" 19 defining a circular aperture 26, with score lines 28 radiating outwardly from the aperture which can separate when medical sharps or other medical wastes are thrust downwardly through the top wall.

The preferred embodiment of the cylindrical housing used for collecting and disposing of medical sharps and other medical wastes is formed of a leak resistant, rigid, combustible material selected from: cellulosic materials, such as paper stock, cardboard, wood, and particle board, non-natural cellulosic materials such as rayon, cellophane, and cellulose-nitrate, and other biodegradable materials such as natural rubber and natural wax, whereby when burned form gases of combustion which yield no more than trace levels of sulfur or chlorine. The cylindrical housing also can be colored by color agents for designating medical sharps, medical wastes, or chemotherapy waste, whereby the coloring agents are also biodegradable. The housing material can include an anti-microbial additive such as a commercially available disinfectant. In addition, it is understood that a cylindrical housing as illustrated in the drawings is only one of many configurations the system for collecting and disposing of medical wastes can take. The housing can be of various sizes and proportions and can be of shapes such as rectangular, octagonal, etc.

FIG. 2 shows a used syringe 29 inserted through the aperture 26 of the telescopic cover 9 and into the holding chamber 12 of the housing 11. The aperture 26 formed in the top wall 19 is sized in accordance with the expected size of the medical waste items to be collected so that the medical sharp or other medical waste must slightly stretch the aperture along the score lines 28 when being inserted in the collector. This tight and yielding fit of the syringe avoids inadvertent escape of the syringe during subsequent removal and collection of the collector. The needle of the syringe which is likely to hold liquid contaminants, usually penetrates an insert or absorption package 30. The absorption package is formed of a group of materials selected from: natural cellulosic, non-natural cellulosic, and other materials which are biodegradable and combustible, with antimicrobial additives, such as commercially available disinfectants. As shown in FIG. 2, this absorption package is placed in the lower portion of the cylindrical housing 11 abutting the bottom plug 15 and the cylindrical side wall 16.

Figure 4:
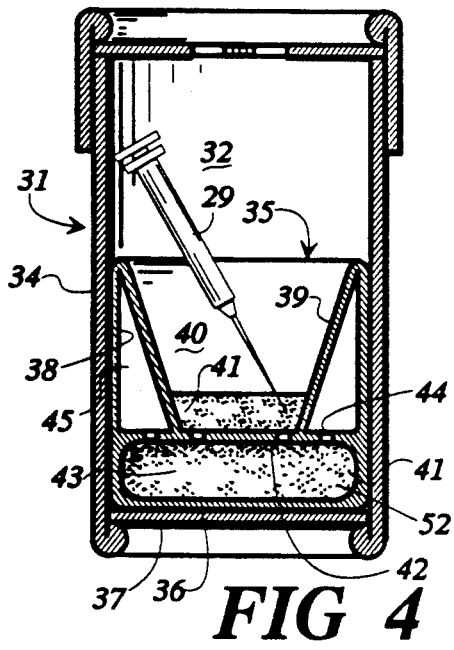
FIG. 4 is a side cross-sectional view of another embodiment and its insert.

FIG. 4 illustrates an additional embodiment of the absorption package of the invention, showing a housing 31 for collecting and disposing of medical sharps and with the absorption package comprising a self-supporting insert 35. The insert fits snugly into the lower portion of the holding chamber 32 of the cylindrical body 34 with a bottom wall 36 of the insert 35 abutting the bottom wall 37 of the housing. The self-supporting insert 35 has an annular outer vertical side wall 38 extending from the bottom wall 36 of the insert, upwards to a height less than or equal to the height of the cylindrical side wall 34. An inwardly and downwardly inclined conically shaped inner wall 39 extends downwardly from the upper edge of the vertical side wall 38 of the insert and intersects horizontal false bottom wall 42 to form a conically shaped receptacle 40, and an annular hollow cavity 45 surrounds the conically shaped receptacle. A cork 41 or other means for being partially penetrated by, and therefore, retaining medical sharps is positioned in the lower portion of the conically shaped receptacle 40. False bottom wall 42 forms lower chamber 43 above bottom wall 36, and absorptive and combustible material 52 is contained in the lower chamber. Thus, the conically shaped receptacle 40 tends to guide the medical wastes inwardly and downwardly toward the cork, etc. 41 in the lower portion of the conically shaped receptacle as the medical sharps and other medical wastes fall downwardly into the receptacle, whereby excess fluids of the wastes will be absorbed by and dispersed in the absorptive and combustible material 52. Multiple air holes 44 are defined in the false bottom wall 42, wherein any excess fluids can have access to the absorption material 52 in the lower chamber 43 to further absorb any fluids emitted from the medical sharps. The air holes 44 also serve as ventilators to enhance combustion within the holding chamber 32, when incinerated.

An additional embodiment of the absorption package or insert comprises free, flowable particulate material which conforms to the shape of the container when dispersed within the container (not shown).

Figure 5:
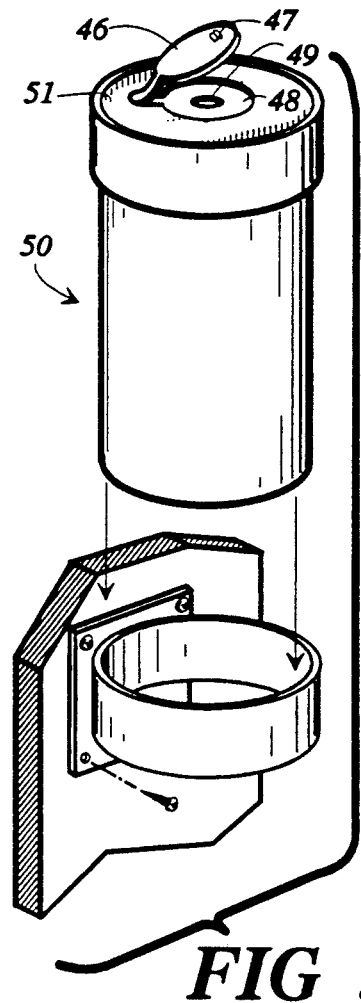
FIG. 5 is a perspective view similar to FIG. 1, but of another embodiment of the invention having a modified lid structure.

FIG. 5 illustrates an additional embodiment 50 of a receptor for medical sharps, wherein the aperture 49 of the top wall 51 is closed by a lid 46 having a tab 47 that can be grasped and pulled upwardly to reveal an inner recessed lip 48 about the aperture 49 for receiving medical waste.

Figure 6:
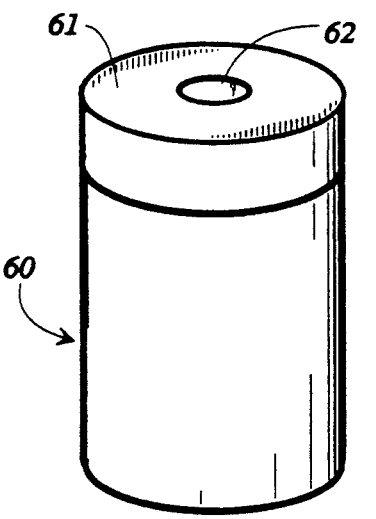
FIG. 6 is a perspective view of a third embodiment of the invention which is of a molded construction.
Figure 7:
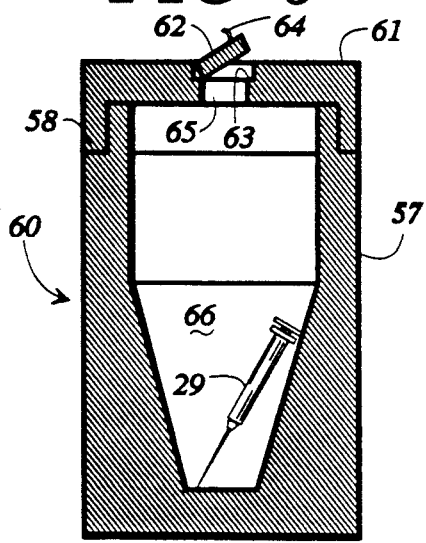
FIG. 7 is a side cross-sectional view of the embodiment of FIG. 6.

FIGS. 6 and 7 illustrate another embodiment of the cylindrical housing 60 which includes a molded monolithic lower housing 57 and a molded top wall or a telescoping cover 61. The cover or top wall 61 defines an aperture 65 and a circular lid 62 which closes the aperture, with the lid 62 having a tab 64 for opening the circular lid. The circular lid 62 abuts an inner recessed flange 63 about the aperture 65.

The housing 60, which can be cylindrical on the outside as shown or other shapes, defines a holding chamber 66 for receiving medical wastes. The inside surfaces can be tapered for funneling the medical sharps 29 and other medical wastes toward a centrally located position, if desired. The lower housing 57 has a recessed annular flange or rim 58 in the upper portion of its annular side wall for receiving the interlocking telescopic cover 61 and the telescopic cover 61 and lower housing 57 form a smooth exterior side wall of the housing 60.

Figure 8:
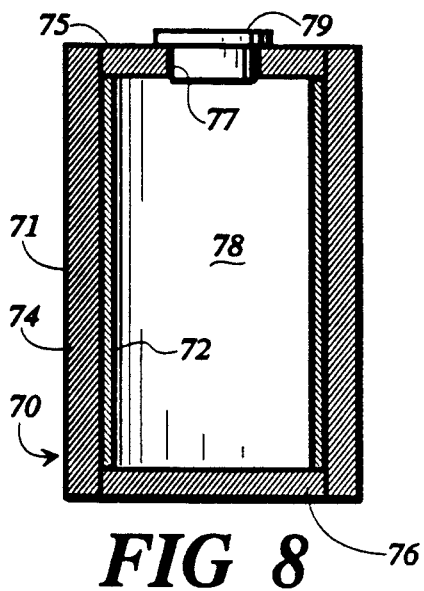
FIG. 8 is a side cross-sectional view of another embodiment, which includes a dual wall construction of the cylindrical housing.

FIG. 8 shows another embodiment 70 of the housing which includes a dual cylindrical sidewall structure 71 having an inner cylindrical side wall 72 and an outer concentric cylindrical side wall 74. The inner side wall 72 is shorter than outer side wall 74 and has its upper and lower ends off set inwardly of the ends of the outer side wall 74. A top wall 75 and a bottom wall 76 supplement the length of the inner side wall 72 at both ends to form smooth ends to the housing for collecting and disposing of medical wastes. A holding chamber 78 is defined by the inner side wall 72, and the top wall 75 and the bottom wall 76. It is understood that the inner side wall 72 and the outer side wall 74 may vary in wall thickness either singly or taken in combination with each other. The top wall 75 defines an aperture 77 and a plug 79 is inserted in and closes the aperture.

Figure 9:
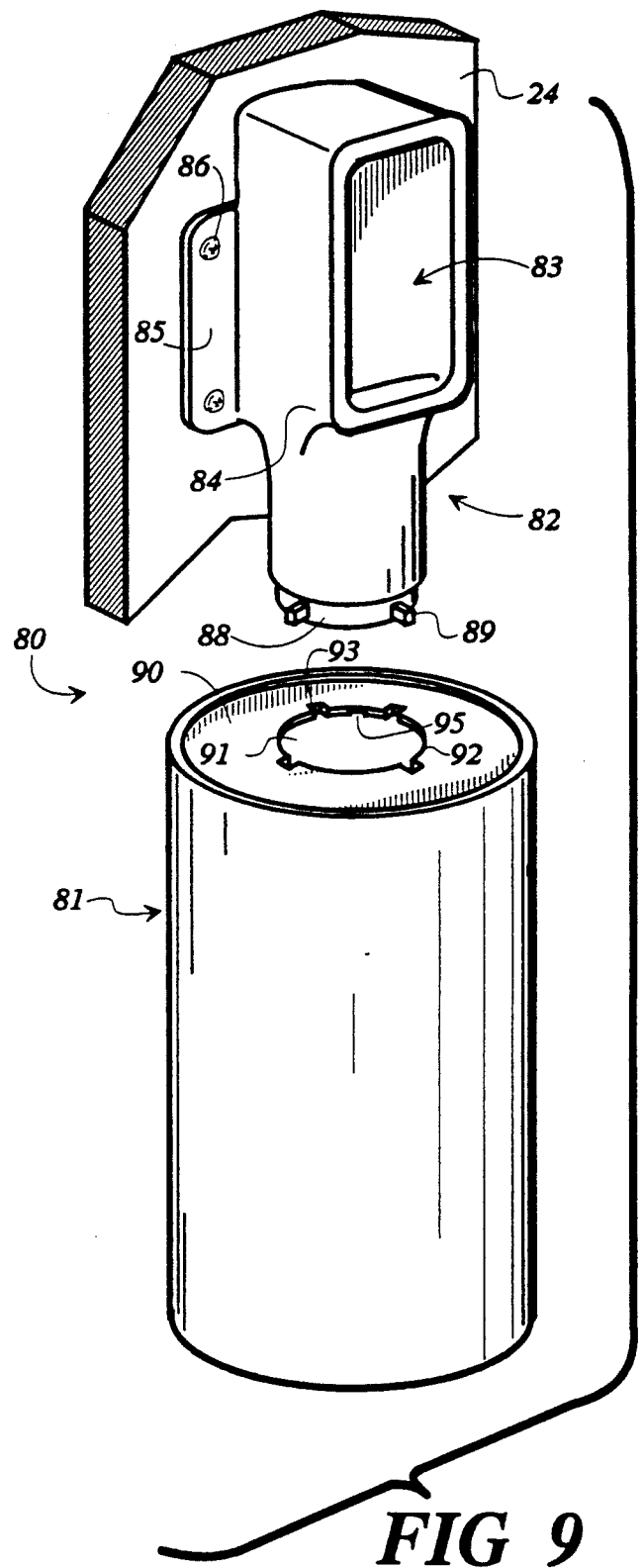
FIG. 9 is an exploded perspective view of yet another embodiment which includes a lid having a vertically oriented opening and a collector housing.

FIG. 9 shows another embodiment 80 of the system, having a head 82 mounted to the wall 24. The head 82 defines an elongated opening 83 and a curved chute 84 extending inwardly and downwardly from the opening toward the cylindrical housing 81 below, which receives the medical sharps. The head 82 has a flange 85 with screws 86 or other fasteners for securing the flange to a wall 24. The lower portion of the head 82 defines a cylindrical collar 88 with multiple protruding studs 89 extending outwardly therefrom for releasably locking together the head 82 and the cylindrical housing 81.

The cylindrical housing 81 includes a top wall 90 having an aperture 91. A rim 92 defines the aperture 91 and has open slots 93 formed therein for receiving the studs 89 of the collar 88 of the head 82 to pass through the top wall, and closed notches 95 to nonrotatably mount the housing on the head 82. Therefore, as medical personnel fill the cylindrical housing, they can see through the transparent or translucent head 82 and downwardly through the opening 83 to determine the volume of medical waste present in the housing 81 and replace the housing as necessary.

FIGS. 10 and 11 illustrate an additional embodiment 100 of the system for collecting and disposing of contaminated wastes, which includes a cylindrical housing 101, having a lower side wall portion 102 and an upper side wall portion 104. The lower cylindrical side wall portion 102 comprises an inwardly turned circular seat 105 with a bottom wall or "plug" 106 positioned inside the lower cylindrical side wall portion 102. The bottom wall 106 is supported on the circular seat 105. The upper side wall porion 104 of the cylindrical housing 101 includes an opening 109 (FIG. 10) leading to a holding chamber 108 for collecting contaminated wastes.

A telescoping member 110 comprises a cylindrical side wall 111 which is of sufficient internal breadth to telescopically fit about the lower side wall portion 102, as well as the upper side wall portion 104. The cylindrical side wall 111 comprises an inwardly turned circular seat 112 which supports an end wall 115.

As seen in FIG. 10, the telescoping member 110 is formed to telescope about the lower side wall portion 102 when the opening 109 is exposed to collect contaminated wastes. The telescoping member 110 thereby provides a stabilizing base for the system 100 as contaminated wastes are being collected in the collector. In a hospital environment, this configuration is most commonly referred to as a "kick bucket" for receiving large volumes of medical wastes, such as surgical masks, drapes, garments, or kit packs in an operating or an emergency room.

FIG. 11 illustrates the telescoping member 110 mounted about the upper side wall portion 1-4 of the system 100. When the telescoping member 110 telescopes about the upper said wall 104, the opening 109 is thereby sealed. Thus, as shown in FIG. 11, the telescoping member 110 provides a cover for the opening 109 of the system so as to provide a secure container for contaminated wastes, especially when the wastes must be handled and transported from one location to another.

The preferred material of construction in all of the above embodiments comprises biodegradable, or otherwise known as non petroleum-based materials selected from the following group: natural cellulosic-based materials such as wood, cardboard, particle board and fiber board, non-natural cellulosic materials, such as rayon, cellophane, and cellulose-nitrate, and other materials, such as natural rubber and natural wax which when burned emit no more than trace amounts of sulphur or chlorine. These materials add to the Btu loading for completely rendering and transforming the contents of the collectors. Additional qualities which can be taken singly or in combination, are absorbent for absorbing liquids emitted from the medical wastes, leak resistant so as to avoid leaking liquid wastes, puncture resistant so as to avoid a needle of a syringe puncturing the wall of the collector, and rigid so as to avoid inadvertent crushing.

FIG. 12 shows an additional embodiment 120 of the system for collecting and disposing of medical wastes including a receptacle 121 having an opening 122 therein, which takes the similar form and function of a generic trash bag. The receptacle 121 is inserted into an opening 125 of any commercially available can or collector 124 and conforms to the shape of its designated collector housing. The receptacle 121 is of an appropriate size to function as a liner for the collector housing and leave a remaining flange about a rim 126 of the collector so as to hold itself in position and to ensure noncontamination of the rim of the collector.

The embodiment 120 can be formed of non-natural cellulosic materials, such as rayon, cellophane, and cellulose-nitrate, whereby when incinerated evolves no more than trace levels of sulfur or chlorine and yields substantially only biodegradable ash. Characteristics of this embodiment include leak-resistance, combustibility, and biodegradability, however, characteristics of this receptor do not necessarily include puncture-resistance and rigidity because of the general structure of the non-natural, cellulosic material. Thus, this embodiment is particularly advantageous for use when discarding chemotherapy, pathological, surgical masks, gloves, drapes, and other non-sharp contaminated wastes.

In some of the above described embodiments, the mass of the material used to form the housing is matched with the volume of the holding chamber which will receive a predetermined mass of syringes and other anticipated typical medical wastes so that the amount of the material of the housing is sufficient to emit enough heat when burned to transform the medical wastes in the holding chamber into a substantially noncontaminated and noncombustible residue or ash. After incineration of the collector housing, the ash of the collector itself will consist of a biodegradable "mineral" ash.

In some of the above described embodiments, geometric variations such as wall thickness and mass of the housing and the insert, can be adjusted relative to the internal collection volume of the holding chamber, to yield a predetermined ratio of the ash of the housing with respect to the ash of the medical waste, when incinerated. This ratio can be adjusted by increasing or decreasing the thickness of the collector walls so as to increase or decrease the weight of the collector, or by changing the size and/or shape of the collector without changing the weight of the collector.

Therefore, if it is desired that the ashes of incineration of the collector and its contents include more paper ash, which is biodegradable, and less plastic ash, which is not biodegradable, the manufacturer of the collector can adjust the size, volume and/or weight of the collector. Thus, the ash content of the collector and its contents can be adjusted so that the ash can be used, for example, as a fertilizer if it contains a high ratio of paper ash, or as an additive to a building material such as concrete or tar if it contains a high ratio of plastic ash.

EXAMPLE

For example when the empty collector is 250 mm high and 100 mm in inside diameter, the available volume is calculated: $h\pi r^2 = 1,963,494$ mm$^3$. If the syringe is 10 mm in outside diameter and 100 mm long, the occupied volume is calculated: $h\pi r^2 = 7,854$ mm$^3$. At 100% packing (theoretical case), 250 syringes fit into the collector's "occupied volume". For a practical case, the packing density is estimated at 25% of the theoretical full packing condition, which is 62 syringes. If each syringe weighs 0.75 ounces, there are 21.33 syringes per pound, so the loaded collector holds 2.93 pounds of syringes. If the empty collector comprises 8 ounces of cardboard, which yields 10% ash by weight, then upon burning the collector, the anticipated burn results of the collector are 0.05 pounds of ash. Assuming the syringes are plastic and yield 1.7% ash by weight, then upon burning, the anticipated burn results of 2.93 pounds of syringes yield 0.05 pounds of ash. Thus, upon burning the collector filled with a practical load of syringes the resulting ratio of plastic ash to paper ash is 1 to 1.

The wall thickness and other geometric variations of the collector housing can be tailored to accommodate the needs of different locations throughout the medical facility, and to accommodate different items to be deposited in the collectors and can be adapted relative to the collection volume within the housing to further control leak-resistance, puncture-resistance, incinerability, biodegradability, and other factors related to the system for collecting and disposing of medical wastes.

Although this invention has been described in relation to medical wastes, it can be used with other types of wastes, particularly any types of contaminated wastes that should be carefully disposed of by burning While this invention has been described in relation to these preferred embodiments, it will be apparent to those skilled in the art that the invention is susceptible to additional embodiments without departing from the spirit and scope of the invention. Therefore, it is intended that the invention not be limited except by the claims.

We claim:

1. A process of burning contaminated wastes comprising:

forming a collector fabricated of materials selected from a group consisting of: natural cellulose materials, non-natural cellulose materials, natural rubber and natural wax, which are combustible and biodegradable, and when burned evolve no more than trace levels of chlorine or sulphur and yield substantially only biodegradable ash, said collector defining a holding chamber for receiving contaminated wastes;

the collector having been formed of a mass of the material which embodies the collector in comparison with the volume of the holding chamber of the collector to yield a predetermined ratio of the ash of combustion of the collector material with respect to the ash of combustion of the anticipated maximum amount of wastes collected in the holding chamber when the collector and the wastes in its holding chamber are burned;

placing the contaminated wastes in the holding chamber of the collector; and combusting in a furnace environment the collector with the contaminated wastes collected in the holding chamber of the collector.

2. The process of claim 1 and wherein the step of placing the contaminated wastes in the holding chamber of the collector further comprises:

depositing medical wastes, including surgical kit pack trays, gowns, masks, garments, gloves and drapes in the holding chamber.

3. The process of claim 1 and wherein the step of forming the collector of a mass of the material which embodies the collector further comprises:

changing the thickness of the material which forms the collector.

* * * * *